US006372445B1

(12) United States Patent
Davis et al.

(10) Patent No.: US 6,372,445 B1
(45) Date of Patent: Apr. 16, 2002

(54) CHROMOPHORES IN THE PREPARATION OF NOVEL TANDEM CONJUGATES

(75) Inventors: Kenneth A. Davis, Woodside; Barnaby Abrams, San Carlos; James A. Bishop, Santa Cruz, all of CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/521,452

(22) Filed: Mar. 7, 2000

Related U.S. Application Data

(63) Continuation of application No. PCT/US98/20831, filed on Oct. 1, 1998, which is a continuation-in-part of application No. 08/943,491, filed on Oct. 3, 1997, now Pat. No. 6,133,429.

(51) Int. Cl.$^7$ .............................................. G01N 33/53
(52) U.S. Cl. ........................ 435/7.24; 435/6; 435/7.5; 435/40.5; 436/501; 436/532; 436/546; 436/800; 530/391.3; 530/391.5; 530/391.9; 530/402; 530/403
(58) Field of Search .................. 8/550, 636; 530/391.3, 530/391.5, 402, 403, 391.9; 436/546, 501, 532, 800; 435/7.24, 6, 405, 7.5

(56) References Cited

U.S. PATENT DOCUMENTS

| 4,520,110 A | | 5/1985 | Stryer et al. ................. 436/501 |
| 4,542,104 A | | 9/1985 | Stryer et al. ................. 436/536 |
| 4,876,190 A | | 10/1989 | Recktenwald .................. 435/7 |
| 4,981,977 A | | 1/1991 | Southwick et al. .......... 548/455 |
| 5,145,772 A | | 9/1992 | Voyta et al. .................... 435/4 |
| 5,171,846 A | | 12/1992 | Gupta ......................... 530/400 |
| 5,597,696 A | | 1/1997 | Linn et al. ...................... 435/6 |
| 5,622,821 A | | 4/1997 | Selvin et al. ................... 435/6 |
| 5,648,213 A | * | 7/1997 | Reddy et al. |
| 5,714,386 A | | 2/1998 | Roederer .................... 436/546 |
| 5,861,256 A | * | 1/1999 | Glass et al. |

FOREIGN PATENT DOCUMENTS

| EP | 0 314 406 B1 | 8/1993 |
| EP | 0 747 700 | 12/1996 |
| EP | 0 800 083 A2 | 4/1997 |

OTHER PUBLICATIONS

S. Mujumdar et al, Bioconjugate Chem., 7, 356–362 (1996).*
H. Gruber et al, Bioconjugate Chem., 8, 552–559 (1997).*
Ballou, et al., "Tumor labeling in vivo using cyanine–conjugated monoclonal antibodies," *Cancer Immunol. Immunother.* 41:257–263 (1995).
Beavis and Pennline, "ALLO–7: A New Fluorescent Tandem Dye for Use in Flow Cytometry," *Cytometry* 24:390–394 (1996).
Chen and Evangelista, "Feasibility Studies for Simultaneous Immunochemical Multianalyte Drug Assay by Capillary Electrophoresis with Laser–Induced Fluorescence," *Clin. Chem.* 40(9):1819–1822 (1994).

(List continued on next page.)

*Primary Examiner*—Mary E. Ceperley
(74) *Attorney, Agent, or Firm*—David W. Highet, Esq.

(57) ABSTRACT

The inventors herein disclose new heterobifunctional chromophores that are capable of coupling with two distinct moieties. One moiety may be either a signal-enhancing agent or a blocking agent. The second moiety may be one member of a specific binding pair. The invention is based in part on the surprising result that when a chromophore is used as a "cross-linker" between a signal-enhancing agent and a member of a binding pair (essentially being buried between the two), the signal of the chromophore is not quenched. This arrangement, wherein the chromophore acts simultaneously as a cross-linker and a detectable compound, provides significant advantages over previously known compounds since the chromophore is sterically hindered from interacting non-specifically with substances present in the test systems. Moreover, the chromophore can be used as a cross-linker with little or no loss of detectable signal.

28 Claims, 4 Drawing Sheets

OTHER PUBLICATIONS

Daubner, et al., "Yellow light emission of *Vibrio fischeri* strain Y–1: Purification and characterization of the energy–accepting yellow fluorescent protein," *Proc. Natl. Acad. Sci. USA* 84:8912–8916 (1987).

Ernst, et al., "Cyanine Dye Labeling Reagents for Sulfhydryl Groups," *Cytometry* 10:3–10 (1989).

Feeney, R.E., "Chemical modification of proteins: comments and perspectives," *Int. J. Peptide Protein Res.* 29:145–161 (1987).

Glazer and Stryer, "Fluorescent Tandem Phycobiliprotein Conjugates," *Biophys. J.* 43:383–386 (1983).

Han, et al., "Chemical Cross–Links of Proteins By Using Bifunctional Reagents," *Int. J. Biochem.* 16(2):129–145 (1984).

Hung, et al., "Cyanine Dyes with High Absorption Cross Section as Donor Chromophores in Energy Transfer Primers," *Analytical Biochemistry* 243:15–27 (1996).

Laso, F., *Cytometry* 26(4):275–280 (1996).

Mujumdar, et al., "Cyanine Dye Labeling Reagents Containing Isothiocyanate Groups," *Cytometry* 10:11–19 (1989).

Mujumdar, et al., "Cyanine Dye Labeling Reagents: Sulfoindocyanine Succinimidyl Esters," *Bioconjugate Chemistry* 4(2):105–111 (1993).

Prasher, et al., "Primary structure of the *Aequorea victoria* green–fluorescent protein," *Gene* 111:229–233 (1992).

Robins, R., "Methods Mol. Biol.," *Immunochemical Protocols 2nd Edition* 80:337–346 (1998).

Rye, et al., "Stable fluorescent complexes of double–stranded DNA with bis–intercalating asymmetric cyanine dyes: properties and applications," *Nucleic Acids Research* 20(11):2803–2812 (1992).

Shapiro, M.D., H.M., "cyanine Dye labels: From Cy–Fi to Hi5 for Cy5," *Practical Flow Cytometry, Third Edition* 281–282 (1995).

Southwick, et al., "Cyanine Dye Labeling Reagents–Carboxymethlindocyanine Succinimidyl Esters," *Cytometry* 11:418–430 (1990).

van Vugt, et al., "Binding of PE–CY5 Conjugates to the Human High–Affinity Receptor for IgG (CD64)," *Blood* 88:2358–2359 (1996).

Waggoner, et al., "PE–CY5 A New Fluorecent Antibody Label for Three–Color Flow Cytometry with a Single Laser," *Ann. N.Y. Acad. Sci.* 677:185–193 (1993).

Yu, et al., "Cyanine dye dUTP analogs for enzymatic labeling of DNA probes," *Nucleic Acids Research* 22(15):3226–3232 (1994).

Zalipsky, S., "Functionalized Poly(ethylene glycol) for Preparation of Biologically Relevant Conjugates," *Bioconjugate Chem.* 6:150–165 (1995).

Zeng, et al., "Fluorescence Energy–Transfer Cyanine Heterodimers with High Affinity for Double–Stranded DNA," *Analytical Biochemistry* 231(1):256–260 (1995).

Zhu, et al., "Directly labeled DNA probes using fluorescent nucleotide with different length linkers," *Nucleic Acids Research* 22(16):3418–3422 (1994).

* cited by examiner

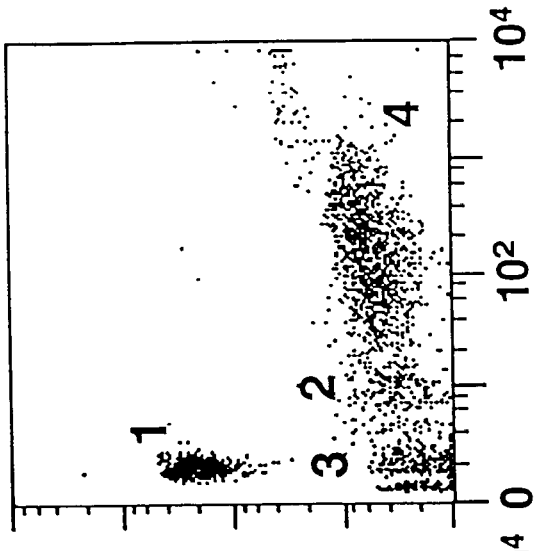
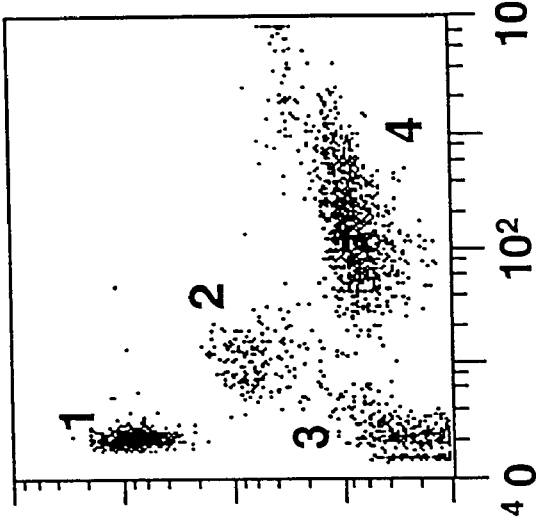
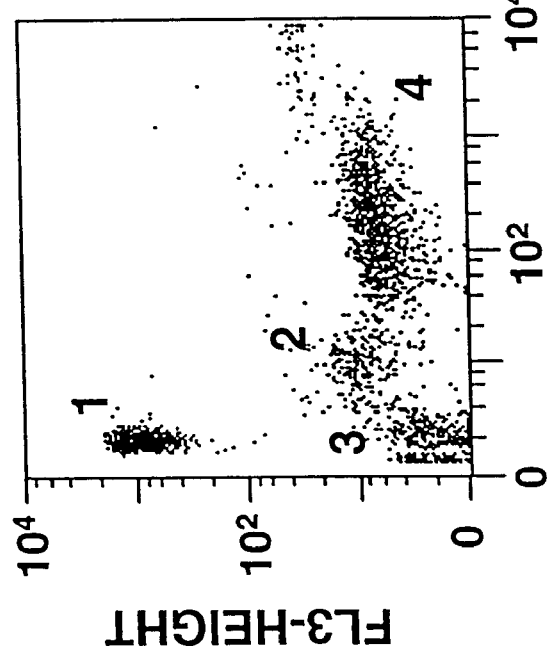

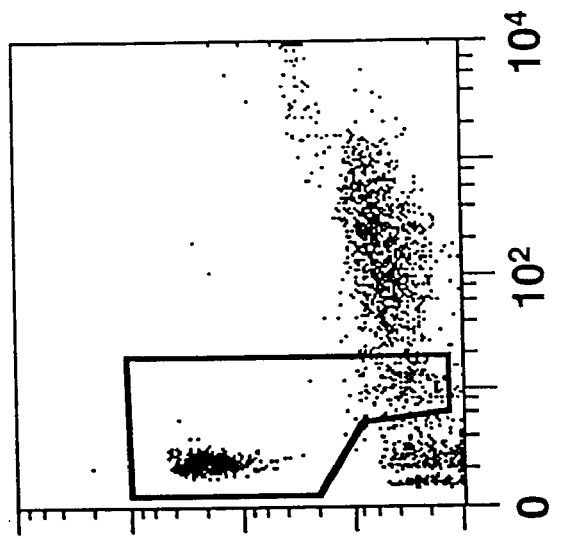
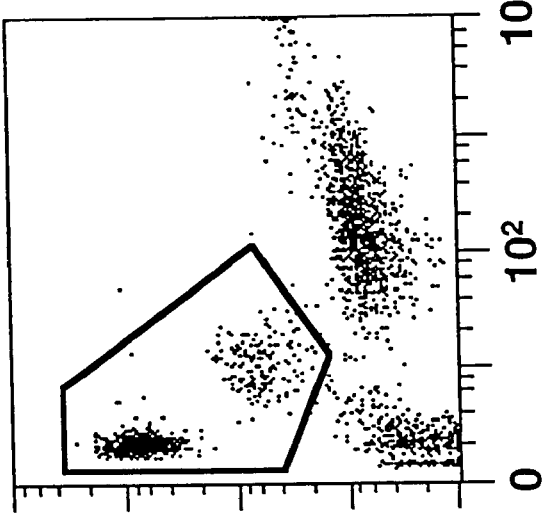
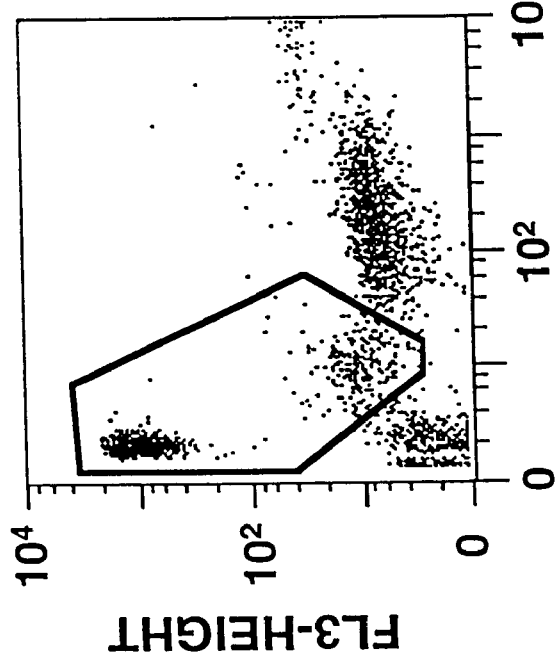

CHROMOPHORES IN THE PREPARATION OF NOVEL TANDEM CONJUGATES

CROSS REFERENCE TO RELATED APPLICATIONS

This application is a continuation of international patent application No. PCT/US98/20831, filed Oct. 1, 1998, which is a continuation-in-part of U.S. patent application Ser. No. 08/943,491, filed Oct. 3, 1997, now U.S. Pat. No. 6,133,429, the disclosures of which are incorporated herein by reference in their entireties.

FIELD OF THE INVENTION

The present invention relates to novel bifunctional chromophores useful for labeling materials such as proteins or cells, novel complexes containing bifunctional chromophores, and methods of using them.

BACKGROUND OF THE INVENTION

Fluorescent labeling reagents have become increasingly useful investigative tools. The wider use of fluorescently labeled probes has resulted partly from advances in instrumentation and partly from the availability of new and improved fluorescent dyes. The cyanine dyes have received particular interest since relatively minor alterations in their chemical structure allows for variation in their excitation and emission wavelengths, an advantage for designing multicolor systems useful for simultaneous detection of more than one fluorescent probe.

More recently the cyanine dyes have become widely used as one component of a tandem conjugate with a second fluor, often proteinaceous fluorophores such as phycoerythrin (PE) or Peridinin-chlorophyll a-protein (PerCP). When the emission spectrum of one fluor overlaps the excitation spectrum of another, and they are sufficiently close to each other (<10 nm), it is possible for the excitation energy of the first fluor to be transferred to the second through a fluorescent resonance energy transfer process (Glazer and Stryer, *Biophys. J.* 43:383–386, 1983).

A significant drawback to the use of these reagents, particularly for labeling antibodies used in analysis and sorting of blood cells, is the tendency for the fluor complex to bind to components of the system in an indiscriminate manner (van Vugt et al., *Blood* 88:2358–2359, 1996; Beavis and Pennline, *Cytometry* 24:390–394, 1996; Shapiro, *Practical Flow Cytometry*, 3rd ed., p. 282, 1995).

A need, therefore, still exists for new labeling reagents that are sensitive, easily detected, and exhibit little or no undesirable fluor-mediated binding.

BRIEF DESCRIPTION OF THE INVENTION

The inventors herein disclose new heterobifunctional chromophores that are capable of coupling with two distinct moieties. One moiety may be either a signal-enhancing agent or a blocking agent. The second moiety may be one member of a specific binding pair. The invention is based in part on the surprising result that when a chromophore is used as a "cross-linker" between a signal-enhancing agent and a member of a binding pair (essentially being buried between the two), the signal of the chromophore is not quenched. This arrangement, wherein the chromophore acts simultaneously as a cross-linker and a detectable compound, provides significant advantages over previously known compounds since the chromophore is sterically hindered from interacting non-specifically with substances present in the analytical system. Moreover, the chromophore can be used as a cross-linker with little or no loss of detectable signal.

Also disclosed are complexes formed between a bifunctional chromophore and a signal-enhancing agent. The signal-enhancing agent is capable of participating in resonance energy transfer reactions. The interaction between the chromophore and the signal-enhancing agent may be covalent or non-covalent. Alternatively, the bifunctional chromophore may form a complex with a blocking agent.

Invention complexes can be used in assays involving non-covalent binding to the complementary member of the specific binding pair. Thus, the present invention should find widespread application since a wide variety of methods involve competitive or non-competitive binding of one member of a binding pair to another for detection, analysis or measurement of the presence of the complementary member of the binding pair.

Similar chromophore complexes known in the art have been widely used but exhibit significant drawbacks including relative dimness (making them unsuitable for detection of complementary binding pair members present at low levels), photobleaching, signal spillover into neighboring detection channels (a critical problem when detecting multiple colors simultaneously), instability, and non-specific binding to irrelevant or inappropriate components of the analytical system. The chromophore and methods of the invention, however, overcome these problems, particularly the problem of non-specific binding.

Also disclosed are methods of making the heterobifunctional chromophores of the invention and methods for making novel complexes having bifunctional chromophores as one of their components. The complexes are suitable for a variety of uses such as the labeling of antibodies for use as immunologic reagents and the labeling of DNA for use as a probe. Tandem complexes available in the art do not employ bifunctional chromophores, wherein the chromophore is buried between the signal enhancing agent and the member of the specific binding pair (Waggoner et al., EP 747700, published Dec. 11, 1996; Stryer et al., U.S. Pat. No. 4,542,105, issued Sep. 17, 1985).

BRIEF DESCRIPTION OF THE DRAWINGS

FIG. 3 compares the chromophore-specific binding to monocytes of CD3-PerCP, CD3-PerCP-Cy5.5 (Cy5.5 "exposed") and CD3-Cy5.5-PerCP (Cy5.5 "buried") (see Example 2). The dot plots of side scatter vs. Fl3 (A-1, B-1 and C-1) show gating of T-lymphocytes and monocytes, which are displayed as an FL3 histogram of PerCP/PerCP-Cy5.5 intensity (A-2, B-2 and C-2). CD3 antibody labeled with Mal/Cy5.5-PerCP complex of the invention shows little or no chromophore-specific binding to monocytes.

DETAILED DESCRIPTION OF THE INVENTION

Figure 1:
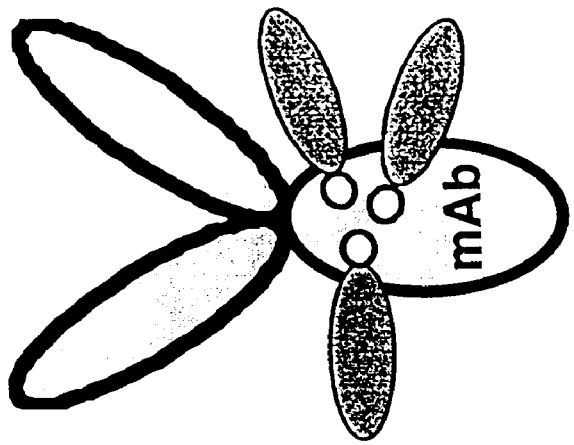
FIG. 1 schematically illustrates the manner in which the conjugates of the invention interact with one component of a binding pair, in this illustration, an antibody. Previously, dye conjugates (e.g., PE-Cy5, PerCP-Cy5.5, APC-Cy7) were bound to the antibody via a cross-linking moiety on the signal-enhancing agent leaving the dye (e.g., Cy5, Cy5.5, Cy7) exposed to its surroundings so that it could interact with vessel walls, cell surfaces, etc. In the conjugates of the invention, the chromophore is bifunctionalized so that it functions both as a detectable dye compound and a crosslinking moiety attaching the chromophore:signal-enhancer complex to the antibody (effectively "burying" the chromophore and blocking its ability to bind non-specifically).
Figure 1:
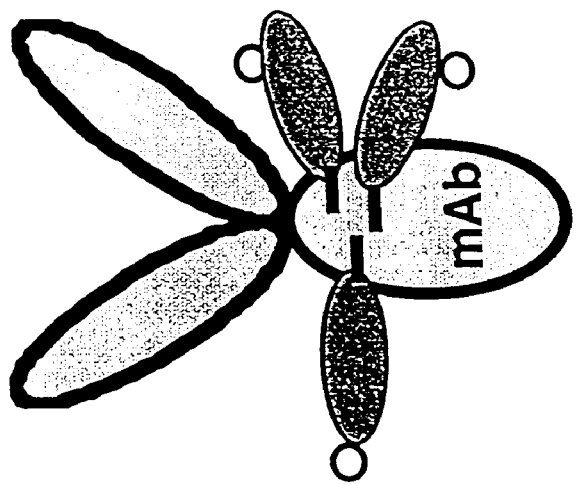
Figure 1:

The invention herein discloses heterobifunctionalized chromophores, wherein one functionality on said chromophore is capable of coupling with a signal-enhancing agent or a blocking agent, and the other functionality is capable of coupling with a member of a specific binding pair.

By "heterobifunctional" it is meant that the chromophore has two different functional groups, each of which is capable of forming a linkage with a second molecule. Suitable examples of functional groups include succinimidyl esters, isothiocyanates, carbodiimide activated carboxyls, hydrazide activated aldehyde imidoesters, maleimides, vinyl sulfones, active halogens, pyridyldisulfides, thiols, and the like.

By "chromophore" it is meant a compound capable of being detected calorimetrically or fluorometrically. The specific examples disclosed herein describe chromophores detected by fluorescence. It should be understood, however, that the compounds and methods described can equally be utilized with chromophores that are detected by other means readily available to those skilled in the art, such as, for example, absorbance or phosphorescence.

Chromophores contemplated for use in the practice of the present invention are detectable compounds having two functional groups, each of which is capable of undergoing a chemical reaction with a second compound such that the chromophore and second compound undergo a chemical interaction. When the two functional groups are the same, the chromophore is referred to herein as "homobifunctional," whereas when the two functional groups are different, the chromophore is referred to herein as "heterobifunctional" (as defined above). In an alternate embodiment of the invention, a monofunctional chromophore can be modified with a trifunctional linker, thereby introducing two available sites of attachment where only one previously existed. The chromophore may be a fluorescent dye, a non-fluorescent dye, or the like. Examples of suitable chromophores include, but are not limited to, fluorescein and its derivatives and the cyanine dyes such as isothiocyanines, merocyanines, indocarbocyanines (e.g., Cy3), benzindocarbocyanines (e.g., Cy3.5), indodicarbo-cyanines (e.g., Cy5), benzindodicarbocyanines (e.g., Cy5.5), indotricarbocyanines (e.g., Cy7), benzindo-dicarbocyanines (e.g., Cy7.5), thiazole orange, oxazole yellow, CYA (3-(epsilon-carboxypentyl)-3' ethyl-5,5'-dimethyloxacarbocyanine), and the like (see, for example, Mujumdar et al., *Bioconjugate Chem.* 4(2):105–111 (1993); Ernst et al., *Cytometry* 10:3–10 (1989); Mujumdar et al., *Cytometry* 10:11–19, 1989; Southwick et al., *Cytometry* 11:418–430, 1990; Hung et al., *Anal. Biochem.* 243(1):15–27, 1996; *Nucleic Acids Res.* 20(11): 2803–2812 (1992); Mujumdar et al., *Bioconjugate Chem.* 7:356–362 (1996); and Southwick and Waggoner, U.S. Pat. No. 4,981,977, issued Jan. 1, 1991, incorporated by reference herein in its entirety).

Cyanine dyes are the presently preferred chromophores for use in the practice of the present invention. Particularly preferred cyanine dyes are the indodicarbocyanines and the indotricarbocyanines. Synthesis of these dyes is described in detail in Mujumdar et al., *Bioconjugate Chem.* 7:356–362, 1996 and Southwick et al., *Cytometry* 11:418–430, 1990. A particularly preferred chromophore is Cy5.5-Bis-OSu (compound X (Cy5.205.OSu) in Mujumdar, 1996, supra). This dye contains two succinimidyl ester reactive groups which can be readily derivatized as described herein. It is understood by those skilled in the art that bifunctional chromophores contemplated for use in the practice of the present invention can be homobifunctional (and thus useful as intermediates for the preparation of heterobifunctional chromophores and/or for the preparation of novel complexes as described herein) or heterobifunctional. Thus, such chromophores can be isolated or synthesized so as to contain two identical reactive groups, one of which can be subsequently modified to create heterofunctionality, if desired. Alternatively the heterobifunctional chromophore can be initially synthesized with different reactive groups.

The chromophores of the invention can be coupled to either a signal-enhancing agent or a blocking agent. By "signal-enhancing agent" it is meant a compound that is capable of forming a complex with the bifunctional chromophore and is additionally capable of emitting a detectable signal, for example, a fluorescent signal.

A suitable signal-enhancing agent, in the case of fluorescing compounds, will be capable of participating in fluorescent resonance energy transfer (FRET) reactions (see, Glazer and Stryer, *Biophys. J.* 43:383–386, 1983). In FRET reactions, a donor molecule becomes excited at a wavelength A and emits radiation at a wavelength B. An acceptor molecule is subsequently excited by the radiation emitted from the donor molecule (wavelength B) and emits at a wavelength C. A fluorescent signal-enhancing molecule useful in the invention can act as either donor molecule or acceptor molecule.

Examples of signal-enhancing agents contemplated for use in the practice of the present invention include, but are not limited to, small organic molecules such as fluorescein and its derivatives, Texas red, rhodamine, umbelliferone, lanthanide chelates, dipyrometheneboron difluoride, Rhodolgreen, proteinaceous fluorophores such as the phycobiliproteins (phycoerythrin (PE), allophycocyanin (APC)), Peridinin-chlorophyll-proteins (PerCP), yellow fluorescent proteins (YFPs), green fluorescent proteins (GFPs), and the like (see Daubner et al., *Proc. Natl. Acad. Sci. USA* 84(24):8912–8916, 1987; Prasher et al., *Gene* 111(2):229–233, 1992; Recktenwald, U.S. Pat. No. 4,876, 190, issued Oct. 24, 1989, and publications cited therein; Stryer et al., U.S. Pat. No. 4,520,110, issued May 28, 1985; Selvin et al., U.S. Pat. No. 5,622,821, issued Apr. 22, 1997).

A particularly preferred signal-enhancing agent is PerCP, which can be isolated from a variety of phytoplankton species. This proteinaceous fluorophore contains a wide range of functional groups for conjugation including amino, and carboxyl groups. PerCP and its isolation is described in detail in Recktenwald, U.S. Pat. No. 4,876,190, issued Oct. 24, 1989, incorporated by reference herein in its entirety. While PerCP itself has some utility as a fluorescent dye, its lack of sensitivity (relative dimness) and its tendency to rapidly bleach when used with a strong laser limit its applicability. The invention complexes are significantly brighter than PerCP alone. For example, the heterobifunctional chromophore-PerCP complex used in the Examples below is approximately five times as bright as PerCP used alone. In addition, this complex does not photobleach under conditions where PerCP alone is photobleached, allowing the complex to be useful in such applications as stream-in-air flow cytometers and fluorescent cells sorters, which generally use stronger lasers.

The chromophores of the invention may alternatively be coupled to a blocking agent. By "blocking agent" it is meant a compound that is capable of forming a complex with a bifunctional chromophore but which is generally unreactive with other substances once the complex is formed. A preferred blocking agent will be capable of reducing the ability of the chromophore to participate in chromophore-mediated undesirable binding. The interaction between the chromophore and the blocking agent may be covalent or non-covalent. A signal-enhancing agent may also be a blocking agent.

Suitable blocking agents are relatively large molecules that are relatively inert. Well known examples of blocking agents used in the art include, but are not limited to, serum proteins such as serum albumins (such as bovine serum albumin) and alpha and gamma globulins; milk proteins such as casein and cellulose; biocompatible polymers such as polyalkylene glycols; and the like. Particularly preferred blocking agents are the polyalkylene oxides (e.g., polyethylene glycols (PEGs)).

PEGs are polyether diols of the general structure HO—$(CH_2—CH_2O)_n$—$CH_2$—$CH_2$—OH. Their desirability as a blocking agent derives from, among other things, their wide range of solubilities in both aqueous and organic media, their relative lack of toxicity and immunogenicity, their nonbiodegradability and their relative inertness once derivatized. They are commercially available in a variety of molecular weights, typically between 1000 and 20,000 Daltons. One of skill in the art would easily be able to select the appropriate size of PEG molecule for use as a blocking agent with the chromophores employed in accordance with the present invention. Monomethyl PEG (mPEG) is often used to prepare conjugates since the presence of only one derivatizable end group on mPEG minimizes crosslinking and improves the homogeneity of PEG-conjugate preparations. A review of functionalized PEGs for the preparation of conjugates can be found in Zalipsky, *Bioconjugate Chem.* 6:150–165 (1995).

The chromophore of the invention is additionally able to couple with a member of a specific binding pair. By "specific binding pair" it is meant a pair of molecules that specifically interact with one another in preference to interaction with any other molecule. The specificity of binding between two molecules can also be judged by the strength of their interaction with one another. Binding pairs are said to exhibit specific binding when they exhibit avidity of at least $10^7$, preferably at least $10^8$, more preferably at least $10^9$ liters/mole. One example of a specific binding pair is an antibody and antigen.

A member of a binding pair suitable for conjugation with a chromophore complex of the invention will comprise at least one functional group(s) capable of coupling to a functional group of a bifunctionalized chromophore with up to 10 or higher being possible. Examples of functional groups include amino, thio, carboxyl, and the like. Binding pairs can include, for example without limitation, antibodies and antigens or haptens, nucleotides (which specifically bind to complementary oligonucleotides when oligomerized), biotin and avidin or streptavidin, ligand and receptors, and the like. The chromophore complex may be coupled to either member of the binding pair as would be appropriate for the intended use of the labeled conjugate.

The chromophores of the invention can couple with a signal-enhancing agent or blocking reagent and member of a binding pair by covalent or non-covalent means. Non-covalent means include electrostatic means, hydrogen bonding, and the like.

Depending on the molecules employed for the preparation of conjugated complexes according to the invention, a wide variety of linking groups may be used for coupling by covalent interactions, both for linking the chromophore to the signal-enhancing agent or blocking agent and linking the chromophore to the member of the binding pair. Suitable functional groups for the bifunctionalized chromophore include, but are not limited to, succinimidyl, isothiocyanate, carbodiimide activated carboxyl, hydrazide activated aldehyde imidoester, and the like, all of which react with amino groups; and maleimide, vinyl sulfone, active halogen, pyridyldisulfide, and the like, all of which react with sulfhydryl; and so on. General discussions of covalent cross-linking using reagents having different functional groups can be found in Han et al., *Int. J. Biochem.* 16(2):129–145, 1984 and Feeney, *Int. J. Peptide Protein Res.* 29:145–161, 1987. Methods of attaching chromophores to oligonucleotides via a linking spacer can be found in Linn et al., U.S. Pat. No. 5,597,696, issued Jan. 28, 1997, incorporated by reference herein in its entirety.

The utility of the chromophores and complexes of the invention is readily recognized by those skilled in the art. The chromophore complexes can be used to label antibodies (polyclonal or monoclonal) which are then useful in a variety of methodologies including fluorescent activated cell sorting or analysis, immunoassays, immunostaining, and the like. Antibody conjugates can also be used for diagnostic purposes, both in vitro and in vivo. Ballou et al., for example, described a method of using antibody conjugates for the detection of tumors in vivo. (Ballou et al., *Cancer Immunol. Immunother.* 41(4) :257–263, 1995.) Lanza et al. describe an in vitro method of diagnosing leukemia using antibody conjugates. (Lanza et al., *Leuk. Lymphoma* 18(Suppl. 1):25–30, 1995.)

Non-antibody proteins can also be labeled with the chromophore complexes disclosed herein. For example, antigens may be coupled with a chromophore complex and used in competitive immunoassays. Protein ligand such as growth factors or cytokines can be labeled with chromophore complexes and subsequently used to study ligand:receptor interactions for either research or clinical purposes.

The complexes of the invention can be used to label a variety of non-protein molecules. Chen and Evangelista, for example, describe a multianalyte drug assay wherein labeled morphine and phencyclidine (PCP) are used in a competitive immunoassay to detect drug levels in urine (Chen and Evangelista, *Clin. Chem.* 40(9):1819–1822, 1994).

Nucleotides or oligonucleotides can be labeled using the chromophore complexes disclosed herein. Individual nucleotide conjugates can be subsequently incorporated into oligonucleotides by nick translation or polymerase chain reaction (PCR) (Zhu et al., *Nucleic Acids Res.* 22(16): 3418–3422, 1994). Alternatively, oligonucleotides can be directly conjugated with the chromophore complexes (Zheng et al., *Anal. Biochem* 231(1):256–260, 1995). The resulting labeled oligonucleotides (by either method) are useful in both research and clinical applications including DNA and RNA hybridization-based diagnostic methods, DNA and RNA sequencing, restriction fragment mapping, fluorescence in situ hybridization (FISH), and the like (see, for example, Zeng et al., supra; Yu et al., *Nucleic Acids Res.*

22(15):3226–3232, 1994; Hung et al., *Anal. Biochem.* 243 (1):15–27, 1996).

The complexes of the invention can be included as reagents in kits (either as starting materials (heterobifunctionalized chromophore and signal-enhancing agent) or pre-formed complexes prepared from homobifunctional or heterobifunctional chromophores) provided for use in, for example, the methodologies described above.

The invention is described in greater detail by reference to the following non-limiting examples.

EXAMPLE 1

Synthesis of Cy5.5-PerCP Employing a Heterobifunctional Chromophore

Twelve volumes of the chromophore Cy5.5-Bis-OSu Reactive Dye (OSu/Cy5.5/OSu) (Amersham Life Science, Cat. No. R15500: 33 mM in dimethyl formamide (DMF)), were added to 8 volumes of DMF, 76 volumes of buffer (20 mM morpholinoethane sulfonic acid (MES), 1 mM ethylene diamine tetraacetic acid (EDTA), pH 7.0), and 4 volumes of 100 mM mercaptoethylamine-HCl (Aldrich Cat. No. 12,292-0). After a 20 minute incubation at room temperature, 9 volumes of 500 mM bis-maleimidotriethylene glycol (Molecular BioSciences Cat. No. 46777) in DMF were added and incubation continued a further 20 minutes at room temperature. The reaction mixture containing the heterobifunctional Cy5.5 (Mal/Cy5.5/OSu) and other reaction products was stored on ice if to be used immediately or at −80° C. for longer term storage.

PerCP, 50 nmoles (1.8 mg, QuantaPhy, Inc.) in 50 mM Na phosphate, 1 mM EDTA pH 8.0 was incubated with 100 nmoles of Mal/Cy5.5/OSu for 30 minutes at room temperature. These conditions were selected to minimize the number of PerCP molecules containing two chromophore molecules. The amino groups of PerCP react with the remaining succinimidyl ester moiety (OSu) of the Mal/Cy5.5/OSu. The Mal/Cy5.5-PerCP complex was separated from free Mal/Cy5.5/OSu and other reaction products by buffer exchange into a buffer containing 0.14 M Na acetate (pH 5.5) and 1 mM EDTA using Sephadex™ G-50. The ratio of Cy5.5 to PerCP was determined by absorption at 280, 478 and 674 nm and found to be 0.6:1.

An antibody specific to T-lymphocytes (CD3(Leu4) Becton Dickinson Immunocytometry Systems) was labeled with Mal/Cy5.5-PerCP by standard means. Briefly, the antibody was derivatized so as to have 6–10 free sulfhydryl moieties per antibody molecule. The reduced antibody was then incubated with a 10 fold excess of Mal/Cy5.5-PerCP, then fractionated by gel filtration on a column containing Superose™ 6. The fractions containing antibody conjugated to "buried" Cy5.5-PerCP (CD3-Cy5.5-PerCP) were pooled and used for further studies.

Antibody labeled with the "exposed" Cy5.5 complex of the prior art was synthesized for comparison with the "buried" Cy5.5 complex of the invention. PerCP was derivatized with maleimide groups using succinimidyl 4-(N-maleimidomethyl)-cyclohexane-1-carboxylate (SMCC, Pierce Biochemical Corp.) to form PerCP/Mal. PerCP/Mal was then coupled to Cy5.5-mono-OSu (Amersham Life-Science Cat. No. R15600) to form Mal/PerCP-Cy5.5. This complex was used to label CD3 antibody as described above. The resulting labeled antibody conjugate (CD3-PerCP-Cy5.5) leaves the cyanine dye exposed.

EXAMPLE 2

Staining of Whole Blood with CD3-Cy5.5-PerCP

Normal human blood (50 μl) containing EDTA was incubated with 38 ng (10 μl) CD3-Cy5.5-PerCP (Cy5.5 buried), CD3-PerCP-Cy5.5 (Cy5.5 exposed), or CD3-PerCP (Becton Dickinson Immunocytometry Systems Cat. #347344) for 30 minutes at 25° C. Lysing solution (1 ml, FACS® Lysing Solution (Becton Dickinson Immunocytometry Systems Cat. No. 349202)) was added and after incubation for 10 minutes at 25° C., the samples were centrifuged (10 minutes at 200×g). The pellet was resuspended in 0.5 ml phosphate buffered saline (PBS)/0.5% bovine serum albumin (BSA) and analyzed with a FACScan™ type flow cytometer using the manufacturer's directions.

Figures 2, 3A, 3B, 3C:
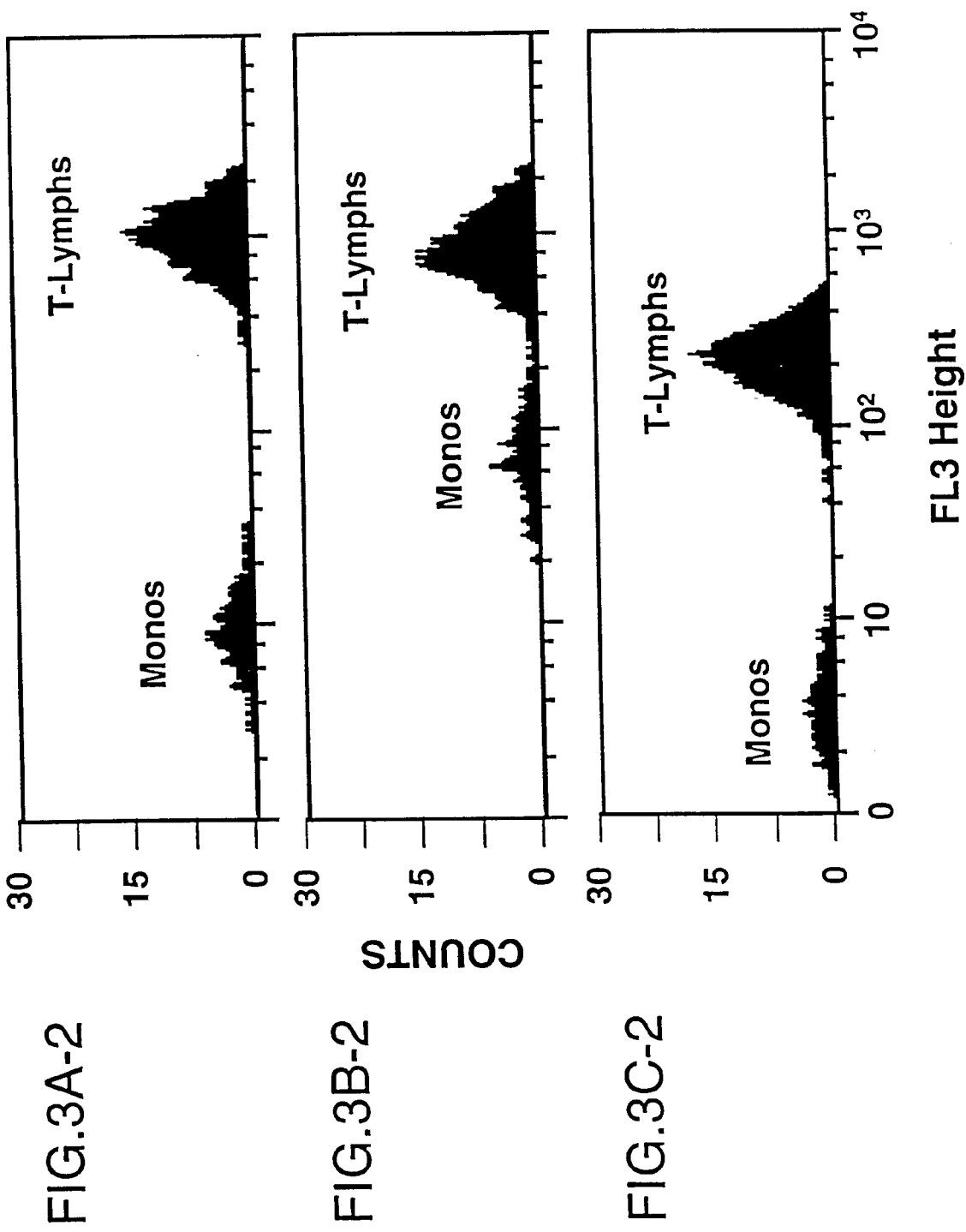
FIG. 2 compares fluorescent staining of whole blood with CD3-PerCP, the prior art CD3-PerCP-Cy5.5 (Cy5.5 "exposed"), and CD3-Cy5.5-PerCP (Cy5.5 "buried") of the invention (see Example 2). CD3 antibody labeled with Mal-Cy5.5-PerCP complex of the invention more effectively differentiates T-lymphocyte populations from other white blood cell populations with lower background than CD3 antibody labeled with Mal/PerCP-Cy5.5 of the prior art. The latter shows strong chromophore (Cy5.5)-mediated binding to monocytes.

The results, shown in FIGS. 2 and 3, demonstrate the superior features of the complexes of the invention. Lymphocytes stained with CD3-Cy5.5-PerCP (Cy5.5 "buried") were approximately five times brighter than lymphocytes stained with CD3-PerCP. Importantly, fluor-specific binding of monocytes was significantly (ten-fold) lower using CD3-Cy5.5-PerCP (Cy5.5 "buried") compared with using CD3-PerCP-Cy5.5 (Cy5.5 "exposed"). In addition, the baseline gap between the monocyte peak and lymphocytes stained with CD3-Cy5.5-PerCP (Cy5.5 "buried") was significantly greater than when stained with either CD3-PerCP-Cy5.5 (Cy5.5 "exposed") or CD3-PerCP (over 1 log vs. 0.1 and 0.9 logs, respectively) demonstrating that different cell populations can be more accurately assessed using the conjugates of the invention.

EXAMPLE 3

Synthesis of Cy5.5-PerCP Employing a Homobifunctional Chromophore

PerCP (12 mg/ml) in 50 mM Na phosphate, 1 mM EDTA pH 8.0 was incubated with 1 mM 2-iminothiolane (Traut's Reagent, Pierce Biochemical Corp.) for 60 minutes at room temperature. The sulfhydryl derivatized PerCP was separated from free iminothiolane and other reaction products by buffer exchange into a buffer containing 50 mM MES and 2 mM EDTA, pH 6.0, using Sephadex™ G-25.

The sulfhydryl derivatized PerCP was incubated with a 2 molar excess of Bis-maleimide Cy5.5 (Amersham Life Science) for 60 minutes at room temperature. The PerCP-Cy5.5-maleimide protein dye complex was separated from unreached dye by buffer exchange into a buffer containing 0.14 M Na acetate pH 5.5 using Sephadex G-50. The ratio of Cy5.5 to PerCP was determined by absorption at 280, 478 and 674 nm and found to be 0.4:1.

An antibody specific to T-lymphocytes (CD3(Leu4) Becton Dickinson Immunocytometry Systems) was labeled with the PerCP-Cy5.5-maleimide complex by standard means. Briefly, the antibody was derivatized so as to have 6–10 free Sulfhydryl moieties per antibody molecule. The Sulfhydryl antibody was then incubated with 10 molar excess of PerCP-Cy5.5-maleimide complex and then fractionated by gel filtration on a column containing Superose™ 6. The fractions containing antibody conjugated through Cy5.5 to PerCP were pooled for further studies. The ratio of PerCP to antibody was determined by absorption as described above and found to be 4.2:1 and the ratio of Cy5.5 to PerCP 0.5:1.

EXAMPLE 4

Alternate Means to Prepare Bifunctional Chromophores

In yet another variation of the chemistry described herein, it is possible to link the chromophore (e.g., Cy5.5) to both the signal enhancing agent (e.g., PerCP) and an antibody through only one end of the chromophore. For example, if a mono-amine version of Cy5.5 is reacted with a compound having one succinimidyl and TWO maleimides (such a molecule is sold by Molecular Biosciences, Boulder Colo., as succinimidyl-3,5-dimaleimidophenyl benzoate), the succinimidyl moiety reacts with the amine moiety in the chromophore, with the net addition of two maleimide moieties to the chromophore, thereby producing a bifunctionalized chromophore. These could be separately linked to signal enhancing agents and antibodies as described herein, thus mediating the conjugation of a signal enhancing agent to an antibody and effectively burying the chromophore between the signal enhancing agent and the antibody.

While the foregoing has been presented with reference to particular embodiments of the invention, it will be appreciated by those skilled in the art that changes in these embodiments may be made without departing from the principles and spirit of the invention, the scope of which is defined by the appended claims.

What is claimed is:

1. A specific binding pair member labeled with a blocked cyanine dye, comprising:
    a specific binding pair member;
    a bifunctionalized cyanine dye having a first and a second functional group; and
    a blocking agent,
    wherein said bifunctionalized cyanine dye couples said specific binding pair member and said blocking agent, and said blocking agent is capable of reducing the binding of said cyanine dye to cell surfaces.

2. The labeled specific binding pair member of claim 1, wherein said specific binding pair member is coupled directly to said cyanine dye's first functional group and said blocking agent is coupled directly to said cyanine dye's second functional group.

3. The labeled specific binding pair member of claim 1, wherein said specific binding pair member is selected from the group consisting of: antibody, antigen, hapten, nucleotides, biotin, avidin, streptavidin, ligands and receptors.

4. The labeled specific binding pair member of claim 3, wherein said binding member is an antibody.

5. The labeled specific binding pair member of claim 1, wherein said bifunctionalized cyanine dye is selected from the group consisting of bifunctionalized Cy3, bifunctionalized Cy3.5, bifunctionalized Cy5, bifunctionalized Cy5.5, bifunctionalized Cy7 and bifunctionalized Cy7.5.

6. The labeled specific binding pair member of claim 1, wherein said cyanine dye is homobifunctionalized.

7. The labeled specific binding pair member of claim 6, wherein said cyanine dye is heterobifunctionalized.

8. The labeled specific binding pair member of claim 7, wherein said cyanine dye is a heterobifunctionalized Cy5.5.

9. The labeled specific binding pair member of claim 1, wherein said blocking agent is selected from the group consisting of a protein, a peptide, an oligonucleotide, a carbohydrate, and a polyalkylene glycol.

10. The labeled specific binding pair member of claim 9, wherein said blocking agent is a protein.

11. The labeled specific binding pair member of claim 10, wherein said protein is selected from the group consisting of serum albumins, alpha globulins, gamma globulins, and casein.

12. The labeled specific binding pair member of claim 9, wherein said blocking agent is a peptide.

13. The labeled specific binding pair member of claim 9, wherein said blocking agent is a carbohydrate.

14. The labeled specific binding pair member of claim 9, wherein said blocking agent is a polyalkylene glycol.

15. The labeled specific binding pair member of claim 14, wherein said polyalkylene glycol is a polyethylene glycol with a molecular weight between 1000 and 20,000 Daltons.

16. The labeled specific binding pair member of claim 1, further comprising a proteinaceous fluorophore, wherein said proteinaceous fluorophore and said cyanine dye are capable of fluorescence resonance energy transfer.

17. The labeled specific binding pair member of claim 16, wherein said proteinaceous fluorophore is selected from the group consisting of: phycobiliproteins, PE, APC, Peridinin-chlorophyll proteins (PerCP), yellow fluorescent proteins, and green fluorescent proteins.

18. The labeled specific binding pair member of claim 16, wherein said specific binding pair member is selected from the group consisting of: antibody, antigen, hapten, nucleotides, biotin, avidin, streptavidin, ligands and receptors.

19. The labeled specific binding pair member of claim 16, wherein said blocking agent is selected from the group consisting of a protein, a peptide, an oligonucleotide, a carbohydrate, and a polyalkylene glycol.

20. The labeled specific binding pair member of claim 16, wherein said bifunctionalized cyanine dye is a selected from the group consisting of bifunctionalized Cy3, bifunctionalized Cy3.5, bifunctionalized Cy5, bifunctionalized Cy5.5, bifunctionalized Cy7 and bifunctionalized Cy7.5.

21. The labeled specific binding pair member of claim 16, wherein said cyanine dye is homobifunctionalized.

22. The labeled specific binding pair member of claim 16, wherein said cyanine dye is heterobifunctionalized.

23. The labeled specific binding pair member of claim 17, wherein said proteinaceous fluorophore is PerCP.

24. The labeled specific binding pair member of claim 23, wherein said binding member is an antibody.

25. The labeled specific binding pair member of claim 24, wherein said cyanine dye is a bifunctionalized Cy5.5.

26. The labeled specific binding pair member of claim 16, wherein said proteinaceous fluorophore is coupled to said cyanine dye's first functional group, said blocking agent is coupled to said cyanine dye's second functional group, and said proteinaceous fluorophore is further coupled to said specific binding member.

27. A method for labeling a specific binding pair member with a blocked cyanine dye, the method comprising:
    using a bifunctionalized cyanine dye to couple a specific binding pair member and a blocking agent,
    wherein said blocking agent is capable of reducing the binding of said cyanine dye to cell surfaces.

28. A method for detecting the presence in a sample of a first member of a specific binding pair, comprising:
    contacting said sample with the labeled specific binding member of claim 1, wherein said labeled binding member is a second, complementary member of said specific binding pair, and then
    detecting the noncovalent binding of said second member to said first member.

* * * * *